United States Patent

Müller et al.

[11] Patent Number: 6,083,970
[45] Date of Patent: Jul. 4, 2000

[54] FUNGICIDAL MIXTURES

[75] Inventors: Ruth Müller, Friedelsheim; Herbert Bayer; Hubert Sauter, both of Mannheim; Eberhard Ammermann, Heppenheim; Gisela Lorenz, Hambach; Siegfried Strathmann, Limburgerhof; Klaus Schelberger, Gönnheim; Maria Scherer, Landau; Joachim Leyendecker, Ladenburg; Bernd Müller, Frankenthal, all of Germany

[73] Assignee: BASF Aktiengesellschaft, Germany

[21] Appl. No.: 09/171,602

[22] PCT Filed: Apr. 3, 1997

[86] PCT No.: PCT/EP97/01668

§ 371 Date: Oct. 22, 1998

§ 102(e) Date: Oct. 22, 1998

[87] PCT Pub. No.: WO97/40672

PCT Pub. Date: Nov. 6, 1997

[30] Foreign Application Priority Data

Apr. 26, 1996 [DE] Germany .................. 196 16 684
Apr. 30, 1996 [DE] Germany .................. 196 17 233
Sep. 2, 1996 [DE] Germany .................. 196 35 518

[51] Int. Cl.⁷ .................. A01N 43/38; A01N 43/56; A01N 43/64
[52] U.S. Cl. .................. 514/407; 514/383; 514/417; 514/421
[58] Field of Search .................. 514/407, 421, 514/417, 383

[56] References Cited

U.S. PATENT DOCUMENTS

| | | | |
|---|---|---|---|
| 2,553,770 | 5/1951 | Kittleson | 167/33 |
| 2,553,771 | 5/1951 | Kittleson | 260/313 |
| 2,553,776 | 5/1951 | Kittleson | 260/326 |
| 5,500,441 | 3/1996 | Wingert et al. | 514/412 |

FOREIGN PATENT DOCUMENTS

| | | |
|---|---|---|
| 645 088 | 3/1995 | European Pat. Off. . |
| 95/21153 | 8/1995 | WIPO . |
| 95/21154 | 8/1995 | WIPO . |
| 96/01256 | 1/1996 | WIPO . |
| 96/01258 | 1/1996 | WIPO . |

OTHER PUBLICATIONS

Research Disclosure Apr. 1993, No. 348, 2244.

*Primary Examiner*—Allen J. Robinson
*Attorney, Agent, or Firm*—Keil & Weinkauf

[57] ABSTRACT

Fungicidal mixtures, comprising
$a_1$) at least one compound from the group selected from oxime ethers of the formula I

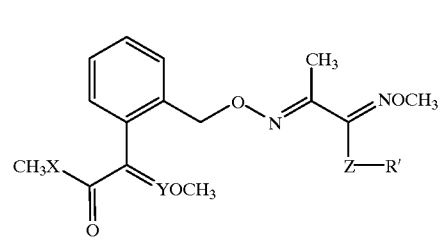

where the substituents have the following meanings:
X is oxygen or amino (NH);
Y is CH or N;
Z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$a_2$) carbamates of the formula II

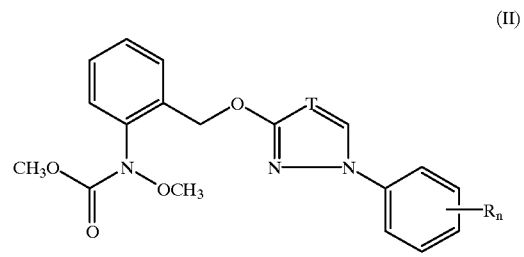

where T is CH or N, n is 0, 1 or 2 and R is halogen, $C_1$–$C_4$-alkyl or $C_1$–$C_4$-haloalkyl, it being possible for the radicals R to be different if n is 2, and
b) a phthalimide derivative selected from the group of the compounds III and IV

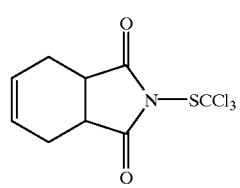

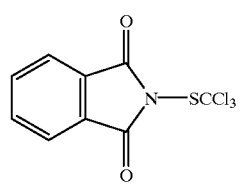

in a synergistically active amount.

17 Claims, No Drawings

FUNGICIDAL MIXTURES

This application is a 371 of PCT/EP97/01668, filed Apr. 3, 1997.

The present invention relates to a fungicidal mixture which comprises at least one compound selected from the group consisting of a$_1$) oxime ethers of the formula I

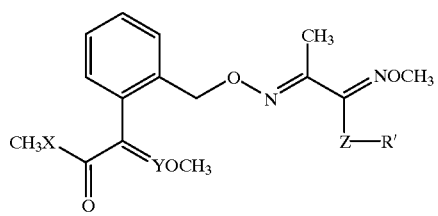

where the substituents have the following meanings:

X is oxygen or amino (NH);

Y is CH or N;

Z is oxygen, sulfur, amino (NH) or $C_1$–$C_4$-alkylamino (N—$C_1$–$C_4$-alkyl);

R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

a$_2$) carbamates of the formula II

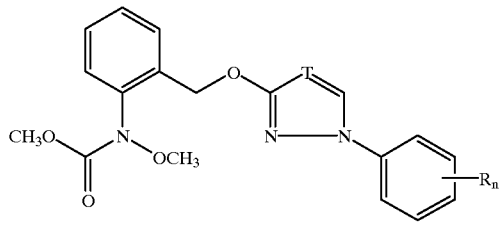

where T is CH or N, n is 0, 1 or 2 and R is halogen, $C_1$–$C_4$-alkyl or $C_1$–$C_4$-haloalkyl, it being possible for the radicals R to be different if n is 2, and b) a phthalimide derivative selected from the group of the compounds III and IV

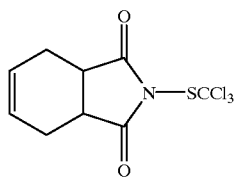

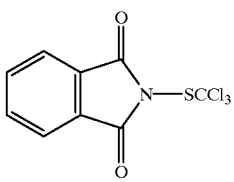

in a synergistically active amount.

Moreover, the invention relates to methods of controlling harmful fungi with mixtures of the compounds I or II and III or of the compounds I or II and IV and to the use of the compounds I, the compounds II and the compounds III and IV for the preparation of such mixtures.

The compounds of the formula I, their preparation and their action against harmful fungi have been disclosed in the literature (WO-A 95/21,153, WO-A 95/21,154, DE-A 195 28 651.0).

The compounds of the formula II, their preparation and their action against harmful fungi have been disclosed in the literature (WO-A 96/01,256 and WO-A 96/01,258).

The phthalimide derivatives III and IV (U.S. Pat. Nos. 2,553,770; 2,553,771; 2,553,776), their preparation and their action against harmful fungi are also disclosed.

It was an object of the present invention to provide mixtures which have an improved activity gainst harmful fungi combined with a reduced total amount of active ingredients applied (synergistic mixtures) with a view to reducing the rates of application and to improving the spectrum of action of the known compounds.

Accordingly, we have found that this object is achieved by the mixture defined at the outset. Moreover, we have found that better control of the harmful fungi is possible by applying the compounds I or II and the compound III or the compound IV simultaneously together or separately or by applying the compounds I or II and the compound III or the compound IV in succession than when the individual compounds are used.

In particular, the general formula I represents oxime ethers in which X is oxygen and Y is CH or X is amino and Y is N.

Moreover, preferred compounds I are those where Z is oxygen.

Equally, preferred compounds I are those where R' is alkyl or benzyl.

Especially preferred with a view to their use in the synergistic mixtures according to the invention are the compounds I compiled in the tables which follow:

Table 1.

Compounds of the formula IA where ZR' for each compound corresponds to one line of Table A

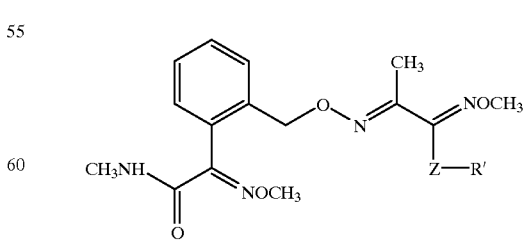

Table 2.

Compounds of the formula IB where ZR' for each compound corresponds to one line of Table A

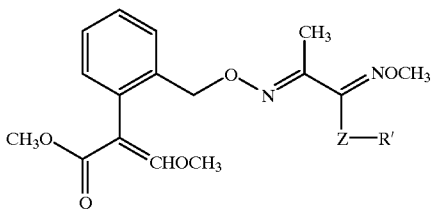

(IB)

TABLE A

| No. | ZR' |
|---|---|
| I.1 | O—CH$_2$CH$_2$CH$_3$ |
| I.2 | O—CH(CH$_3$)$_2$ |
| I.3 | O—CH$_2$CH$_2$CH$_2$CH$_3$ |
| I.4 | O—CH(CH$_3$)CH$_2$CH$_3$ |
| I.5 | O—CH$_2$CH(CH$_3$)$_2$ |
| I.6 | O—C(CH$_3$)$_3$ |
| I.7 | S—C(CH$_3$)$_3$ |
| I.8 | O—CH(CH$_3$)CH$_2$CH$_2$CH$_3$ |
| I.9 | O—CH$_2$C(CH$_3$)$_3$ |
| I.10 | O—CH$_2$C(Cl)=CCl$_2$ |
| I.11 | O—CH$_2$CH=CH—Cl(trans) |
| I.12 | O—CH$_2$C(CH$_3$)=CH$_2$ |
| I.13 | O—CH$_2$-(cyclopropyl) |
| I.14 | O—CH$_2$—C$_6$H$_5$ |
| I.15 | O—CH$_2$—[4-F—C$_6$H$_4$] |
| I.16 | O—CH$_2$CH$_3$ |
| I.17 | O—CH(CH$_2$CH$_3$)$_2$ |

In relation to the C=Y double bond, the compounds of the formula I can be in the E or the Z configuration (in relation to the carboxylic acid function). Accordingly, they can be used in the mixture according to the invention in each case either in the form of the pure E or Z isomer or else in the form of an E/Z isomer mixture. The E/Z isomer mixture or the E isomer are preferably used, the E isomer being especially preferred.

The C=N double bonds of the oxime ether groups in the side chain of the compounds I can be in each case in the form of pure E or Z isomers or in the form of E/Z isomer mixtures. The compounds I can be used in the mixtures according to the invention as isomer mixtures or else as pure isomers. With a view to their use, compounds I which are particularly preferred are those where the terminal oxime ether group in the side chain is in the cis configuration (OCH$_3$ group to ZR').

In particular, formula II represents carbamates where the combination of substituents corresponds to one line of the following table:

TABLE 3

| No. | T | R$_n$ |
|---|---|---|
| II.1 | N | 2-F |
| II.2 | N | 3-F |
| II.3 | N | 4-F |
| II.4 | N | 2-Cl |
| II.5 | N | 3-Cl |
| II.6 | N | 4-Cl |
| II.7 | N | 2-Br |
| II.8 | N | 3-Br |
| II.9 | N | 4-Br |
| II.10 | N | 2-CH$_3$ |
| II.11 | N | 3-CH$_3$ |
| II.12 | N | 4-CH$_3$ |
| II.13 | N | 2-CH$_2$CH$_3$ |

TABLE 3-continued

| No. | T | R$_n$ |
|---|---|---|
| II.14 | N | 3-CH$_2$CH$_3$ |
| II.15 | N | 4-CH$_2$CH$_3$ |
| II.16 | N | 2-CH(CH$_3$)$_2$ |
| II.17 | N | 3-CH(CH$_3$)$_2$ |
| II.18 | N | 4-CH(CH$_3$)$_2$ |
| II.19 | N | 2-CF$_3$ |
| II.20 | N | 3-CF$_3$ |
| II.21 | N | 4-CF$_3$ |
| II.22 | N | 2,4-F$_2$ |
| II.23 | N | 2,4-Cl$_2$ |
| II.24 | N | 3,4-Cl$_2$ |
| II.25 | N | 2-Cl, 4-CH$_3$ |
| II.26 | N | 3-Cl, 4-CH$_3$ |
| II.27 | CH | 2-F |
| II.28 | CH | 3-F |
| II.29 | CH | 4-F |
| II.30 | CH | 2-Cl |
| II.31 | CH | 3-Cl |
| II.32 | CH | 4-Cl |
| II.33 | CH | 2-Br |
| II.34 | CH | 3-Br |
| II.35 | CH | 4-Br |
| II.36 | CH | 2-CH$_3$ |
| II.37 | CH | 3-CH$_3$ |
| II.38 | CH | 4-CH$_3$ |
| II.39 | CH | 2-CH$_2$CH$_3$ |
| II.40 | CH | 3-CH$_2$CH$_3$ |
| II.41 | CH | 4-CH$_2$CH$_3$ |
| II.42 | CH | 2-CH(CH$_3$)$_2$ |
| II.43 | CH | 3-CH(CH$_3$)$_2$ |
| II.44 | CH | 4-CH(CH$_3$)$_2$ |
| II.45 | CH | 2-CF$_3$ |
| II.46 | CH | 3-CF$_3$ |
| II.47 | CH | 4-CF$_3$ |
| II.48 | CH | 2,4-F$_2$ |
| II.49 | CH | 2,4-Cl$_2$ |
| II.50 | CH | 3,4-Cl$_2$ |
| II.51 | CH | 2-Cl, 4-CH$_3$ |
| II.52 | CH | 3-Cl, 4-CH$_3$ |

The compounds II.12, II.23, II.32 and II.38 are especially preferred.

Due to their basic character, the compounds I and II are capable of forming adducts or salts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carboxylic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphonic acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can in this case be in the various valences which they can assume. When preparing the mixtures, it is preferred to employ the pure active ingredients I and II or III and IV, with which further active ingredients against harmful fungi or other pests such as insects, arachnids or nematodes, or else herbicidal or growth-regulating active ingredients or fertilizers can be admixed, if so desired.

The mixtures of the compounds I and/or II and III, or I and/or II and IV, or the simultaneous joint or separate use of the compounds I and/or II and III, or I and/or II and IV, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants such as cotton, vegetable species (eg. cucumbers, beans and curcubits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: Erysiphe graminis (powdery mildew) on cereals, Erysiphe cichoracearum and Sphaerotheca fuliginea on curcubits, Podosphaera leucotricha on apples, Puccinia species on cereals, Rhizoctonia species on cotton, rice and lawn, Ustilago species on cereals and sugar cane, Venturia inaequalis (scab) on apples, Helminthosporium species on cereals, Septoria nodorum on wheat, Botrytis cinerea (gray mold) on strawberries, vegetables, ornamentals and grapevines, Cercospora arachidicola on peanuts, Pseudocercosporella herpotrichoides on wheat and barley, Pyricularia oryzae on rice, Phytophthora infestans on potatoes and tomatoes, Pseudoperonospora species on cucurbits and hops, Plasmopara viticola on grapevines, Alternaria species on vegetables and fruit, and Fusarium and Verticillium species.

Furthermore, they can be used in the protection of materials (eg. in the protection of wood), for example against Paecilomyces variotii.

The compounds I and/or II and III, or I and/or II and IV, can be applied simultaneously together or separately or in succession, the sequence, in the case of separate application, generally not having any effect on the result of the control measures.

The compounds I and/or II and III, or I and/or II and IV, are normally used in a weight ratio of from 1:1 to 1:100, preferably 1:1 to 1:50, in particular 1:3 to 1:30 (I or II:III or IV).

The application rates of the mixtures according to the invention are generally from 0.02 to 5 kg/ha, preferably 0.05 to 3.5 kg/ha, in particular 0.1 to 3.5 kg/ha, depending on the nature of the desired effect.

In the case of the compounds I and/or II, the application rates are customarily from 0.005 to 0.5 kg/ha, preferably 0.01 to 5 kg/ha, in particular 0.01 to 0.3 kg/ha.

Correspondingly, in the case of the compounds III, or the compounds IV, the application rates are from 0.1 to 5 kg/ha, preferably 0.1 to 3.5 kg/ha.

For seed treatment, the application rates of the mixture are generally from 0.001 to 50 g/kg seed, preferably 0.01 to 10 g/kg, in particular 0.01 to 5 g/kg.

If phytopathogenic harmful fungi are to be controlled, the separate or joint application of the compounds I and/or II and III, or I and/or II and IV, or of the mixtures of the compounds I and/or II and III, or I and/or II and IV is effected by spraying or dusting the seeds, the plants or the soils before or after sowing of the plants, or before or after plant emergence.

The fungicidal synergistic mixtures according to the invention, or the compounds I and/or II and III, or I and/or II and IV, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ether, alkylaryl polyether alcohols, isotridecyl alcohol, fatty alcohol/ethylene oxide condensates, ethoxylated castor oil, polyoxyethylene or polyoxyphopylene alkyl ethers, lauryl alcohol polyglycol ether acetate, sorbitol esters, ligninsulfite waste liquors or methylcellulose.

Powders, materials for spreading and dusts can be prepared by mixing or jointly grinding the compounds I and/or II or III, or I and/or II or IV, or the mixture of the compounds I and/or II and III, or I and/or II and IV, with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I and/or II or III, or I and/or II or IV, or of the mixture of the compounds I and/or II and III, or I and/or II and IV. The active ingredients are employed in a purity of from 90% to 100%, preferably 95% to 100% (according to NMR spectrum or HPLC).

The compounds I and/or II or III, or I and/or II or IV, or the mixtures, or the corresponding formulations, are applied by treating the harmful fungi or the plants, seeds, soils, areas, materials or spaces to be kept free from them with a fungicidally active amount of the mixture, or of the compounds I and/or II and III, or I and/or II and IV, in the case of separate application. Application can be effected before or after infection by the harmful fungi.

The fungicidal activity of the compounds and of the mixtures is demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Evaluation was carried out by determining the infected leaf areas in percent. These percentages were converted into efficacies. The expected efficacies of the mixtures of the active ingredients are determined using Colby's formula [R.S. Colby, Weeds 15, 20–22 (1967)] and compared with the observed efficacies.

Colby's formula:

$$E = x + y - x \cdot y / 100$$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b The efficacy (w) is calculated as follows using Abbot's formula:

$$W = (1 - \alpha) \cdot 100 / \beta$$

α is the fungal infection of the treated plants in % and β is the fungal infection of the untreated (control) plants in An efficacy of 0 means that the infection level of the treated plants corresponds to that of the untreated control plants; an efficacy of 100 means that the treated plants are not infected.

EXAMPLES 1 TO 21
Efficacy against Botrytis cinerea on bell peppers

After 4 to 5 leaves had developed properly, bell pepper seedlings cv. "Neusiedler Ideal Elite" were sprayed to run-off with an aqueous suspension made with a stock solution of 10% active ingredient, 63% cyclohexanone and 27% emulsifier. The next day, the treated plants were inoculated with a spore suspension of Botrytis cinerea containing $1.7 \times 10^6$ spores/ml in a 2% strength aqueous Biomalz solution. The test plants were subsequently placed into a controlled-environment cabinet at 22 to 24° C. and high atmospheric humidity. After 5 days, the extent of fungal development on the leaves was determined visually in %.

The results are shown in Table 4.

TABLE 4

| Ex. | Active ingredient | Concentration of active ingredient in the spray mixture in ppm | Efficacy in % of the untreated control |
|---|---|---|---|
| 1V | Control (untreated) | (Disease level 99%) | 0 |
| 2V | A = Tab. 1 A, No. 2 | 50 | 0 |
|  |  | 25 | 0 |
|  |  | 12.5 | 0 |
| 3V | B = Tab. 1 A, No. 4 | 50 | 0 |
|  |  | 25 | 0 |
|  |  | 12.5 | 0 |

TABLE 4-continued

| Ex. | Active ingredient | Concentration of active ingredient in the spray mixture in ppm | Efficacy in % of the untreated control |
|---|---|---|---|
| 4V | III = Captan | 25 | 0 |
|  |  | 12.5 | 0 |
| 5V | IV = Folpet ® | 25 | 0 |
|  |  | 12.5 | 0 |

TABLE 5

| Ex. | Mixture: active ingredient concentration in the spray mixture in ppm | Observed efficacy | Calculated efficacy* |
|---|---|---|---|
| 6 | 50 A + 25 III | 70 | 0 |
| 7 | 25 A + 12.5 III | 30 | 0 |
| 8 | 25 A + 25 III | 97 | 0 |
| 9 | 12.5 A + 12.5 III | 50 | 0 |
| 10 | 50 A + 25 IV | 90 | 0 |
| 11 | 25 A + 12.5 IV | 20 | 0 |
| 12 | 25 A + 25 IV | 97 | 0 |
| 13 | 12.5 A + 12.5 IV | 20 | 0 |
| 14 | 50 B + 25 III | 80 | 0 |
| 15 | 25 B + 12.5 III | 40 | 0 |
| 16 | 25 B + 25 III | 95 | 0 |
| 17 | 12.5 B + 12.5 III | 30 | 0 |
| 18 | 50 B + 25 IV | 90 | 0 |
| 19 | 25 B + 12.5 IV | 80 | 0 |
| 20 | 25 B + 25 IV | 80 | 0 |
| 21 | 12.5 B + 12.5 IV | 70 | 0 |

*calculated using Colby's formula

EXAMPLES 22 TO 42
Efficacy against Botrytis cinerea on bell pepper fruits

Disks of green bell pepper fruits were sprayed to run-off with an aqueous preparation of active ingredient prepared with a stock solution composed of 10% active ingredient, 63% cyclohexanone and 27% emulsifier. 2 hours after the spray coating had dried on, the fruit disks were inoculated with a spore suspension of Botrytis cinerea containing 1.7 X 106 spores per ml of a 2% strength Biomalz solution. The inoculated fruit disks were subsequently incubated for 4 days in humid chambers at 18C. The infected fruit disks were subsequently evaluated visually for botrytis infection.

TABLE 6

| Ex. | Active ingredient | Concentration of active ingredient in the spray mixture in ppm | Efficacy in % of the untreated control |
|---|---|---|---|
| 22V | Control (untreated) | (Disease level 99%) | 0 |
| 23V | A | 200 | 29 |
|  |  | 100 | 50 |
|  |  | 25 | 19 |
| 24V | B | 12.5 | 9 |
|  |  | 50 | 50 |
|  |  | 25 | 39 |
|  |  | 12.5 | 9 |
| 25V | III = Captan | 100 | 19 |
|  |  | 25 | 9 |
|  |  | 12.5 | 9 |
| 26V | IV = Folpet | 100 | 29 |
|  |  | 25 | 9 |
|  |  | 12.5 | 0 |

TABLE 7

| Ex. | Mixture: active ingredient concentration in the spray mixture in ppm | Observed efficacy | Calculated efficacy* |
| --- | --- | --- | --- |
| 27 | 200 A + 100 III | 95 | 43 |
| 28 | 25 A + 12.5 III | 60 | 27 |
| 29 | 100 A + 100 III | 90 | 59 |
| 30 | 25 A + 25 III | 50 | 27 |
| 31 | 200 A + 100 IV | 95 | 50 |
| 32 | 25 A + 12.5 IV | 39 | 19 |
| 33 | 25 A + 25 IV | 60 | 27 |
| 34 | 12.5 A + 12.5 IV | 29 | 9 |
| 35 | 50 B + 25 III | 85 | 54 |
| 36 | 25 B + 12.5 III | 70 | 45 |
| 37 | 50 B + 50 III | 97 | 59 |
| 38 | 25 B + 25 III | 80 | 45 |
| 39 | 50 B + 25 IV | 85 | 54 |
| 40 | 25 B + 12.5 IV | 85 | 39 |
| 41 | 25 B + 25 IV | 85 | 45 |
| 42 | 12.5 B + 12.5 IV | 70 | 9 |

*calculated using Colby's formula

The results of Examples 1 to 42 indicate that the observed efficacy for all mixing ratios exceeds the efficacy precalculated using Colby's formula.

EXAMPLES 43 TO 58
Efficacy against Botrytis cinerea on bell peppers

After 4 to 5 leaves had developed properly, bell pepper seedlings cv. "Neusiedler Ideal Elite" were sprayed to run-off with an aqueous suspension made with a stock solution of 10% active ingredient, 63% cyclohexanone and 27% emulsifier. The next day, the treated plants were inoculated with a spore suspension of Botrytis cinerea containing $1.7 \times 10^6$ spores/ml in a 2% strength aqueous Biomalz solution. The test plants were subsequently placed into a controlled-environment cabinet at 22 to 24° C. and high atmospheric humidity. After 5 days, the extent of fungal development on the leaves was determined visually in %.

TABLE 8

| Ex. | Active ingredient | Concentration of active ingredient in the spray mixture in ppm | Efficacy in % of the untreated control |
| --- | --- | --- | --- |
| 43V | Control (untreated) | (Disease level 99%) | 0 |
| 44V | C = Compound No. II.32 | 50 | 80 |
|  |  | 25 | 80 |
|  |  | 12.5 | 50 |
| 45V | D = Compound No. II.38 | 50 | 30 |
|  |  | 25 | 30 |
|  |  | 12.5 | 0 |
| 46V | III = Captan | 25 | 0 |
|  |  | 12.5 | 0 |
| 47V | IV = Folpet ® | 25 | 0 |
|  |  | 12.5 | 0 |

TABLE 9

| Ex. | Active ingredient concentration in the spray mixture in ppm | Observed efficacy | Calculated efficacy* |
| --- | --- | --- | --- |
| 48 | 50 C + 25 III | 97 | 80 |
| 49 | 25 C + 25 III | 99 | 80 |
| 50 | 50 C + 25 IV | 90 | 80 |
| 51 | 25 C + 25 IV | 97 | 80 |
| 52 | 12.5 C + 12.5 IV | 95 | 50 |
| 53 | 25 D + 25 III | 98 | 29 |
| 54 | 12.5 D + 12.5 III | 97 | 0 |
| 55 | 50 D + 25 IV | 95 | 29 |
| 56 | 25 D + 12.5 IV | 70 | 29 |
| 57 | 25 D + 25 IV | 98 | 29 |
| 58 | 12.5 D + 12.5 IV | 85 | 0 |

*calculated using Colby's formula

EXAMPLES 59 TO 79
Efficacy against Botrytis cinerea on bell pepper fruits

Disks of green bell pepper fruits were sprayed to run-off with an aqueous preparation of active ingredient prepared with a stock solution composed of 10% active ingredient, 63% cyclohexanone and 27% emulsifier. 2 hours after the spray coating had dried on, the fruit disks were inoculated with a spore suspension of Botrytis cinerea containing 1.7 x 106 spores per ml of a 2% strength Biomalz solution. The inoculated fruit disks were subsequently incubated for 4 days in humid chambers at 18° C. The infected fruit disks were subsequently evaluated visually for botrytis infection.

TABLE 10

| Ex. | Active ingredient | Concentration of active ingredient in the spray mixture in ppm | Efficacy in % of the untreated control |
| --- | --- | --- | --- |
| 59V | Control (untreated) | (Disease level 99%) | 0 |
|  | C = Comp. II.32 of Table 3 | 100 | 50 |
|  |  | 25 | 50 |
| 60V | C = Comp. II.32 of Table 3 | 100 | 50 |
|  |  | 25 | 50 |
| 61v | D = Comp. II.38 of Table 3 | 50 | 39 |
|  |  | 25 | 39 |
|  |  | 12.5 | 9 |
| 62V | III = Captan | 200 | 29 |
|  |  | 100 | 19 |
|  |  | 50 | 9 |
|  |  | 25 | 9 |
|  |  | 12.5 | 9 |
| 63V | IV = Folpet ® | 100 | 29 |
|  |  | 50 | 19 |
|  |  | 25 | 9 |
|  |  | 12.5 | 0 |

| Ex. | Active ingredient concentration in the spray mixture in ppm | Observed efficacy | Calculated efficacy* |
| --- | --- | --- | --- |
| 64 | 100 C + 50 III | 95 | 59 |
| 65 | 25 C + 12.5 III | 80 | 54 |
| 66 | 100 C + 100 III | 95 | 59 |
| 67 | 25 C + 25 II | 90 | 54 |
| 68 | 100 C + 50 IV | 90 | 59 |
| 69 | 25 C + 12.5 IV | 80 | 50 |
| 70 | 100 C + 100 IV | 95 | 64 |
| 71 | 25 C + 25 IV | 70 | 54 |
| 72 | 200 D + 100 III | 80 | 43 |
| 73 | 50 D + 25 III | 60 | 18 |
| 74 | 50 D + 50 III | 90 | 27 |
| 75 | 25 D + 25 III | 80 | 18 |
| 76 | 100 D + 50 IV | 80 | 35 |

TABLE 10-continued

| 77 | 50 D + 25 IV | 50 | 18 |
| 78 | 100 D + 100 IV | 80 | 43 |
| 79 | 25 D + 25 IV | 50 | 18 |

*calculated using Colby's formula

The results of the examples indicate that the observed efficacy for all mixing ratios exceeds the efficacy precalculated using Colby's formula.

We claim:

1. A fungicidal composition comprising a) at least one carbamate of the formula II

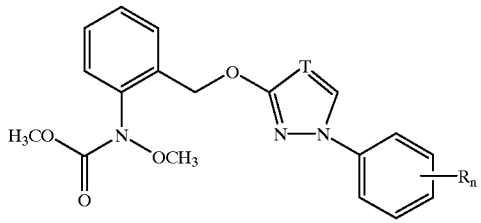

(II)

where T is CH or N, n is 0, 1 or 2 and R is halogen, $C_1$–$C_4$-alkyl or $C_1$–$C_4$-haloalkyl, it being possible for the radicals R to be different if n is 2, and b) a phthalimide of the formula III or IV

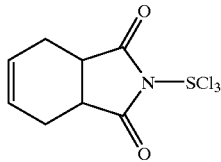

III

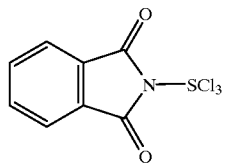

IV in a synergistically effective amount.

2. The fungicidal composition defined in claim 1, comprising the phthalimide of the formula III.

3. The fungicidal composition defined in claim 1, comprising the phthalimide of the formula IV.

4. The fungicidal composition defined in claim 1 wherein the weight ratio of the carbamate to the phthalimide is 1:1 to 1:100.

5. The fungicidal composition defined in claim 1 wherein T is CH.

6. The fungicidal composition defined in claim 1 wherein R is halogen.

7. The fungicidal composition defined in claim 1 wherein T is CH and R is halogen.

8. The fungicidal composition defined in claim 2 wherein T is CH and R is halogen.

9. A method of controlling harmful fungi, which comprises treating the harmful fungi, their environment, or the plants, seeds, areas, materials or spaces to be kept free from said fungi with a synergistically effective amount of a carbamate as set forth in claim 1 and a phthalimide of the formula III or IV as set forth in claim 1.

10. The method defined in claim 9, wherein from 0.005 to 0.5 kg/ha of the carbamate are applied.

11. The method defined in claim 9, wherein from 0.1 to 5 kg/ha of the phthalimide are applied.

12. The method defined in claim 9 wherein the phthalimide is of the formula III.

13. The method defined in claim 11 wherein the phthalimide is of the formula III.

14. The method defined in claim 9 wherein T is CH.

15. The method defined in claim 9 wherein R is halogen.

16. The method defined in claim 9 wherein T is CH and R is halogen.

17. The method defined in claim 10 wherein T is CH and R is halogen.

* * * * *